United States Patent [19]
Sugise et al.

[11] Patent Number: 5,466,858
[45] Date of Patent: Nov. 14, 1995

[54] METHOD OF PRODUCING STRAIGHT-CHAIN ACRYLONITRILE DIMERS

[75] Inventors: Ryoji Sugise; Kouichi Kashiwagi; Masashi Shirai; Toshihiro Shimakawa, all of Ube, Japan

[73] Assignee: Ube Industries, Ltd., Yamaguchi, Japan

[21] Appl. No.: 298,113

[22] Filed: Aug. 30, 1994

[30] Foreign Application Priority Data

| Sep. 3, 1993 | [JP] | Japan | 5-220266 |
| Sep. 3, 1993 | [JP] | Japan | 5-220268 |
| Sep. 3, 1993 | [JP] | Japan | 5-220270 |
| Jul. 5, 1994 | [JP] | Japan | 6-153278 |

[51] Int. Cl.⁶ ............................... C07C 253/30
[52] U.S. Cl. ............................................. 558/364
[58] Field of Search ............................. 558/364

[56] References Cited

U.S. PATENT DOCUMENTS

| 4,519,954 | 5/1985 | Burrington et al. | 558/361 |
| 4,526,884 | 7/1985 | Tsou et al. | 558/361 X |
| 4,681,968 | 7/1987 | Tsou et al. | 558/361 |
| 5,332,844 | 7/1994 | Sugise et al. | 558/364 |

FOREIGN PATENT DOCUMENTS

| 559168 | 8/1993 | European Pat. Off. |  |
| 44-24585 | 10/1969 | Japan . |  |
| 45-4048 | 2/1970 | Japan . |  |
| 47-6290 | 2/1972 | Japan . |  |
| 47-27917 | 2/1972 | Japan . |  |
| 49-28489 | 7/1974 | Japan . |  |
| 51-146420 | 12/1976 | Japan . |  |
| 54-12450 | 5/1979 | Japan . |  |
| 40286918 | 11/1993 | Japan | 558/364 |
| 406092923 | 4/1994 | Japan | 558/364 |
| 1079696 | 8/1967 | United Kingdom . |  |
| 1098726 | 1/1968 | United Kingdom . |  |
| 1168958 | 10/1969 | United Kingdom . |  |
| 1177059 | 11/1970 | United Kingdom . |  |
| 1398089 | 6/1975 | United Kingdom . |  |

*Primary Examiner*—Joseph Paul Brust
*Attorney, Agent, or Firm*—Burgess, Ryan and Wayne

[57] ABSTRACT

Straight-chain acrylonitrile dimers including 1,4-dicyanobutene, 1,4-dicyanobutadiene and adiponitrile are produced at a high selectivity by dimerizing acrylonitrile in the presence of a ruthenium catalyst, and in the presence of a straight-chain dimer selectivity-enhancing agent comprising at least one member selected from (A) substituted benzoic acids, except for monoalkylbenzoic acids, having at least one substituent and preferably exhibiting a pKa of 1.50 to 6.0 determined in water at an ionic strength of 0 to 0.1 mole/liter at 25° C.;

(B) hetero atom-containing acyclic carboxylic acids having at least one substituent having a sulfur or nitrogen atom attached to a carbon atom located in an α- on β-position with respect to a carboxyl group in a main hydrocarbon structure; and (C) 5 to 12 membered heterocyclic carboxylic acids having an oxygen, sulfur or nitrogen atom included in a 5 to 12 membered heterocyclic structure and a carboxyl or carboxymethyl group attached to a carbon atom located in an α-position with respect to the hetero atom.

23 Claims, No Drawings

METHOD OF PRODUCING STRAIGHT-CHAIN ACRYLONITRILE DIMERS

BACKGROUND OF THE INVENTION

1. Field of the Invention

The present invention relates to a method of producing straight-chain acrylonitrile dimers. More particularly, the present invention relates to a method of producing straight-chain acrylonitrile dimers including 1,4-dicyanobutene, 1,4-dicyanobutadiene and adiponitrile in the presence of a ruthenium catalyst at a high selectivity.

The above-mentioned straight-chain acrylonitrile dimers are useful as an intermediate for producing hexamethylenediamine (which is an important material for producing nylon 66), rust-inhibiting agents and vulcanization promoters for rubber materials.

2. Description of Related Art

A method of producing 1,4-dicyanobutene compounds and adiponitrile by using a catalyst comprising a ruthenium compound is well-known from A. Misono et al., Bull. Chem. Soc. Jpn., 41 (1968), 396–401. In this method, acrylonitrile is dimerized in the presence of a ruthenium catalyst in an atmosphere containing hydrogen gas, Misono et al., disclose that if this method is carried out without using the hydrogen gas atmosphere, no dimerization of acrylonitrile occurs, and the dimerization of acrylonitrile can proceed only within the hydrogen-containing gas atmosphere. This method is, however, disadvantageous in that acrylonitrile is brought into contact with the ruthenium catalyst in the presence of hydrogen, wherein dimerization of acrylonitrile proceeds and simultaneously hydrogenation of acrylonitrile, which is not desired, occurs as a side reaction and a large amount of propionitrile is produced as a by-product.

JP-B-44-24,585, JP-B-45-4,048 and JP-B-54-12,450 disclose methods of producing straight-chain acrylonitrile dimers with an enhanced selectivity in the presence of hydrogen. In these methods, the selectivity of the straight-chain acrylonitrile dimers is 55 to 67%. Nevertheless, since the dimerization of acrylonitrile in these methods is carried out in the presence of hydrogen, it is unavoidable that propionitrile be produced as a by-product at a high selectivity of 33 to 45%.

JP-A-51-146,420 discloses a method of dimerizing acrylonitrile at a reaction temperature of 300° C. to 600° C. in the presence of a ruthenium catalyst in the absence of hydrogen. Nevertheless, this method is disadvantageous in that to restrict the by-production of propionitrile and to enhance the selectivity of acrylonitrile to the target straight-chain dimers thereof it is necessary to restrict the conversion of acrylonitrile to the dimers to a level of several percent. When the conversion is enhanced, the by-production of the undesired propionitrile is increased and the selectivity of acrylonitrile to the target dimers is reduced. Further, in this case, the resultant dinitrile product comprises a mixture of straight-chain dimers and branched-chain dimers. Accordingly, the method of the Japanese publication is unsatisfactory.

As mentioned above, the conventional methods for dimerizing acrylonitrile are disadvantageous in that a by-product, for example, propionitrile, which is difficult to return to acrylonitrile, is produced in a large amount, and thus the selectivity of acrylonitrile to the target dimers is reduced, or in that the resultant dimerization product consists of a mixture of straight-chain dimers and branched-chain dimers and thus the selectivity to the target straight-chain dimers becomes low, or in that the use of hydrogen causes an undesirable high risk of explosion when the reaction system is mixed with air or oxygen, and thus specific means for ensuring complete safety for the reaction apparatus and procedures is necessary, and thus the reaction apparatus and procedures become complicated and costly.

SUMMARY OF THE INVENTION

An object of the present invention is to provide a method of producing straight-chain acrylonitrile dimers including 1,4-dicyanobutene, 1,4-dicyanobutadiene and adiponitrile at a high conversion rate, while restricting the production of propionitrile and β-cyanoethyl carboxylate, which are undesirable by-products.

Another object of the present invention is to provide a method of producing straight-chain acrylonitrile dimers including 1,4-dicyanobutene, 1,4-dicyanobutadiene and adiponitrile at a high selectivity without using hydrogen.

The above-mentioned object can be attained by the method of the present invention for producing straight-chain acrylonitrile dimers including 1,4-dicyanobutene, 1,4-dicyanobutadiene, and adiponitrile, which comprises dimerizing acrylonitrile in the presence of a catalyst comprising at least one ruthenium compound and in the additional presence of a straight-chain dimer selectivity-enhancing agent comprising at least one member selected from the group consisting of:

(A) substituted benzoic acids having a benzene ring structure, and a carboxyl group and at least one additional substituent attached to the benzene ring structure, the substituted benzoic acids excepting monoalkylbenzoic acids;

(B) hetero atom-containing acyclic carboxylic acids having a main hydrocarbon structure having 1 to 6 carbon atoms, a carboxyl group attached to a carbon atom in the main hydrocarbon structure, and at least one additional substituent having a hetero atom selected from the group consisting of sulfur and nitrogen atoms, the hetero atom of the additional substituent being attached to a carbon atom contained in the main hydrocarbon structure and located in an α or β-position with respect to the carboxyl group; and (C) five to twelve membered heterocyclic carboxylic acids having a 5 to 12 membered heterocyclic structure including hetero atom selected from the group consisting of oxygen, sulfur and nitrogen atoms and a carboxyl or carboxymethyl group attached to a carbon atom contained in the heterocyclic structure and located in an α-position with respect to the hetero atom.

With respect to the straight-chain dimer selectivity enhancing agent, the substituted benzoic acids (A) preferably have at least one additional substituent selected from the group consisting of halogen atoms, haloalkyl groups, a cyano group, acyl groups, carboalkoxyl groups, aryl groups, alkoxyl groups, an amino group, alkylthio groups and alkylsulfinyl groups. Also, the substituted benzoic acids (A) preferably exhibit a pKa of 1.50 to 6.0, determined in water at an ionic strength of 0 to 0.1 mole/liter at a temperature of 25° C.

In the hetero atom-containing acyclic carboxylic acid (B), the additional substituent is preferably selected from those of the formulae:

—SR$^1$, and —NR$^2$R$^3$ wherein $R^1$, $R^2$ and $R^3$ respectively and independently from each other represent a member selected from the group consisting of a hydrogen atom, alkyl groups having 1 to 15 carbon atoms, alkenyl groups having 2 to 15 carbon atoms, aryl groups having 6 to 15 carbon atoms, acyl groups having 2 to 15 carbon atoms and carboalkoxyl groups having 2 to 15 carbon atoms.

In the 5 to 12 membered heterocyclic carboxylic acids (C), the 5 to 12 membered heterocyclic structure is preferably selected from the group consisting of furan, thiophene and pyrrolidine structures which may be substituted with at least one substituent different from the carboxyl and carboxymethyl groups.

Preferably, the straight-chain dimer selectivity-enhancing agent is present in a molar amount of 0.0001 to 5 times the molar amount of acrylonitrile.

DESCRIPTION OF PREFERRED EMBODIMENTS

The inventors of the present invention energetically investigated a method of producing straight-chain acrylonitrile dimers in the presence of a ruthenium catalyst and in the absence of hydrogen, which method is free from the above-mentioned disadvantages of the conventional methods, and discovered that the straight-chain acrylonitrile dimers can be produced with a high selectivity by dimerizing acrylonitrile in the presence of the ruthenium catalyst, in the absence of hydrogen and in the additional presence of a straight-chain dimer selectivity-enhancing agent consisting of at least one specific carboxylic acid which is contributory to significantly preventing the by-production of not only propionitrile but also carboxylic acid β-cyanoethylesters which are undesirably produced in the presence of conventional carboxylic acids. The present invention was completed based on the above-mentioned discovery.

Namely, in the method of the present invention, the production of propionitrile as an undesirable by-product is significantly restricted.

Further, in the method of the present invention, since the dimerization of acrylonitrile is carried out without using hydrogen, there is no risk of an explosion occurring as a result of mixing hydrogen with air or oxygen and thus it is not necessary to completely seal the reaction system.

In the dimerization of acrylonitrile in accordance with the method of the present invention, a reactor is charged with acrylonitrile, a ruthenium compound catalyst and a straight-chain dimer selectivity-enhancing agent. The reaction mixture is heated to a predetermined reaction temperature and maintained at this reaction temperature for a predetermined reaction time, while agitating the reaction mixture.

In the method of the present invention, the reaction temperature is preferably from 70° C. to 220° C., more preferably from 100° C. to 180° C. When the reaction temperature is too low, the reaction rate becomes too low. Also, when the reaction temperature is too high, the catalyst is rapidly deactivated.

There is no restriction to the reaction pressure. Usually, the reaction pressure can be controlled with in a wide range of from a reduced pressure of 50 mmHg to a high pressure of 100 kg/cm$^2$G. The dimerization of acrylonitrile in accordance with the method of the present invention can be carried out continuously by flowing acrylonitrile through the continuous reactor under a reduced pressure or intermittently in a close reactor under pressure.

The reaction time is variable depending on the reaction temperature and pressure and type and the amount of catalyst. Usually, the reaction time is 0.01 to 30 hours.

In the method of the present invention, the dimerization of acrylonitrile may be carried out in a reaction medium or without using the reaction medium. Nevertheless, the reaction medium is effectively used to control the reaction rate. The reaction medium preferably comprises at least one member selected from nitrile compounds, for example, acetonitrile and propionitrile; sulfoxide compounds, for example, dimethyl sulfoxide and tetramethylene sulfoxide; ether compounds, for example, diethylether and diisopropylether; hydrocarbon compounds, for example, hexane and toluene; amide compounds, for example, acetamide, and N,N-dimethylacetamide; halogenated hydrocarbon compounds, for example, chloroform and carbon tetrachloride; ester compounds, for example, methyl acetate and ethyl acetate; alcohol compounds, for example methyl alcohol and ethyl alcohol; and water.

In the method of the present invention, the ruthenium compound for the catalyst is preferably selected from the group consisting of ruthenium salts of inorganic acids, ruthenium salts of organic acids and ruthenium coordination compounds in which a ruthenium atom serves as a coordination center atom. The inorganic acid ruthenium salts include, for example, ruthenium chloride, ruthenium bromide, ruthenium iodide, ruthenium sulfate, and ruthenium nitrate.

The organic acid ruthenium salts include, for example, ruthenium acetate, ruthenium propionate, ruthenium butanoate, ruthenium pentanoate, ruthenium hexanoate, ruthenium stearate, ruthenium naphthenate, ruthenium oxalate, and ruthenium succinate. Also, the ruthenium coordinate compounds include, for example, dichloro-tetrakis-(dimethylsulfoxide)ruthenium, dichloro-tetraacrylnitrile ruthenium, dichloro-tris(triphenylphosphine)ruthenium, dichloro-tetrakis(triphenylphosphine)ruthenium, and tris-(dimethylsulfoxide)ruthenium, di(2-thiophenecarboxylate-)monohydrate.

The catalyst usable for the present invention may comprise a ruthenium compound alone or a mixture of two or more ruthenium compounds.

In the method of the present invention, the ruthenium compound catalyst is preferably present in an amount of 0.0001 to 10 molar %, more preferably 0.001 to 5 molar %, based on the molar amount of acrylonitrile.

In the method of the present invention, optionally the dimerization of acrylonitrile is carried out in the further presence of at least one member selected from basic compounds and reducing compounds. Those compounds effectively promote the dimerization of acrylonitrile.

The basic compounds are preferably selected from the group consisting of hydroxides of alkali metals, for example, sodium hydroxide, potassium hydroxide, and lithium hydroxide; carbonates of alkali metals, for example, sodium carbonate and potassium carbonate; alkali metal hydrogen carbonates, for example, hydrogen sodium carbonate; alkali metal salts of carboxylic acids, for example, sodium acetate and sodium propionate; alkoxides of alkali metals, for example, sodium methoxide and sodium ethoxide; ammonia; monoalkyl amines, for example, methyl amine and ethylamine; dialkyl amines, for example, dimethylamine and diethylamine; trialkylamines, for example, trimethylamine and triethylamine; aniline; monoalkylanilines, for example, methylaniline and ethylaniline; and dialkylaniline, for example, dimethylaniline and diethylaniline.

The basic compounds may be employed alone or in a mixture of two or more thereof. Preferably, the basic compounds are present in an amount 0.05 to 30 times, more preferably, 0.1 to 20 times the molar amount of the ruthenium compound catalyst.

The reducing compounds usable for the method of the present invention should be capable of reducing the ruthenium compounds contained in the reaction system of the present invention, and are preferably selected from organic reducing compounds, for example, organic tin compounds, organic germanium compounds, organic silicon compounds, organic boron compounds, and organic aluminum compounds; and inorganic reducing compounds, for example, hydrogenated boron compounds, hydrogenated aluminum compounds, metal-hydrogen compounds, and metal elements. The reducing compounds may be employed alone or in a mixture of two or more thereof.

Preferable reducing compounds for the present invention are organic tin compounds, for example, trimethyl stannane [HSnMe$_3$], triethylstannane [HSnEt$_3$], tri-n-propylstannane [HSn(n-pr)$_3$], tri-n-butylstannane [HSn(n-Bu)$_3$], triphenylstannane [HSnPh$_3$], and di-n-propylstannane [H$_2$Sn(n-Pr)$_2$], di-n-butylstannane [H$_2$Sn(n-Bu)$_2$] and diphenylstannane [H$_2$SnPh$_2$]; organic germanium compounds, for example, trimethylgermane [HGeMe$_3$], triethylgermane [HGeEt$_3$], tri-n-propylgermane [HGe(n-Pr)$_3$], metal hydrides, for example, sodium hydride [NaH], sodium borohydride [NaBH$_4$], lithium borohydride [LiBH$_4$], and lithium aluminum hydride [LiAlH$_4$]; metallic sodium, metallic magnesium and metallic zinc.

These reducing compounds may be employed alone or in a mixture of two or more thereof.

Preferably, the reducing compounds are employed in an amount 0.05 to 30 times, more preferably, 0.1 to 20 times, the molar amount of the ruthenium compound catalyst.

When the basic compounds and/or the reducing compounds are employed in insufficient quantities, the resultant dimerization-promoting effect becomes too low. Also, when an excessive amount of those compounds is used, acrylonitrile in the reaction system is not effectively consumed and thus the yield of the intended acrylonitrile dimers is reduced.

In an embodiment of the method of the present invention, the dimerization of acrylonitrile is carried out in the presence of a ruthenium compound catalyst, in the additional presence of a straight-chain dimer selectivity-enhancing agent comprising at least one specific carboxylic acid.

In an embodiment of the method of the present invention, the substituted benzoic acids (A), which except monoalkylbenzoic acids therefrom, are usable as the straight chain dimer selectivity-enhancing agent. The substituted benzoic acids (A) have a benzene ring structure, and a carboxyl group and at least one additional substituent atom or group attached to the benzene ring structure. Monoalkylbenzoic acids are not included in the substituted benzoic acids (A) usable for the present invention.

The additional substituent is preferably selected from the group consisting of halogen atoms, for example, fluorine, chlorine, and bromine atoms, haloalkyl groups, for example, trifluoromethyl group, a cyano group, acyl groups, for example, acetyl group and benzoyl group, carboalkoxy groups, for example, carbomethoxy group, aryl groups, for example, phenyl group, alkoxyl groups, for example, methoxyl group, an amino group, N-substituted amino groups alkylthio groups, for example, methylthio group and alkylsulfinyl groups, for example, methylsulfinyl group.

Preferably, the substituted benzoic acids (A) exhibit a pKa of 1.50 to 6.0, more preferably 1.50 to 5.5, still more preferably 1.80 to 5.5, determined in water at an ionic strength of 0 to 0.1 mole/liter at a temperature of 25° C. When the pKa is less than 1.50, the resultant substituted benzoic acids sometimes cause the dimerization rate of acrylonitrile to be reduced. Also, when the pKa is more than 6.0, the resultant substituted benzoic acid needs to be employed in a large amount to progress the dimerization of acrylonitrile, the β-cyanoethyl carboxylate is produced in a large amount, and thus the selectivity of acrylonitrile to the target straight-chain dimers is reduced.

The substituted benzoic acids (A) usable for the method of the present invention are preferably selected from, for example, fluorobenzoic acids, for example, o-fluorobenzoic acid, m-fluorobenzoic acid, 2,4-difluorobenzoic acid, 2,5-difluorobenzoic acid, 2,6-difluorobenzoic acid, 3,4-difluorobenzoic acid and 3,5-difluorobenzoic acid; chlorobenzoic acids, for example o-chlorobenzoic acid, m-chlorobenzoic acid, 2,3-dichlorobenzoic acid, 2,4-dichlorobenzoic acid, 2,5-dichlorobenzoic acid, 2,6-dichlorobenzoic acid, 3,4-dichlorobenzoic acid and 3,5-dichlorobenzoic acid; bromobenzoic acids, for example, o-bromobenzoic acid, and m-bromobenzoic acid; fluoroalkylbenzoic acids, for example, o-trifluoromethylbenzoic acid and m-trifluoromethylbenzoic acid; chloroalkylbenzoic acids, for example, o- and m-trichloromethylbenzoic acids; cyanobenzoic acids, for example, o-cyanobenzoic acid, m-cyanobenzoic acid, p-cyanobenzoic acid, 2,4-dicyanobenzoic acid, and 3,4-dicyanobenzoic acid; acylbenzoic acids, for example, o-acetylbenzoic acid, m-acetylbenzoic acid and p-acetylbenzoic acid, o-benzoylbenzoic acid, 2-(p-toluoyl)benzoic acid, 2-(4-chlorobenzoyl)benzoic acid; carboxyalkoxybenzoic acids, for example, o-carbomethoxybenzoic acid, m-carbomethoxybenzoic acid, p-carbomethoxybenzoic acid, and 3,4-dicarbomethoxybenzoic acid; arylbenzoic acids, for example, o-phenylbenzoic acid and o-tolylbenzoic acid; aminobenzoic acids, and N-substituted aminobenzoic acids, for example, anthranilic acid, N-methylanthranilic acid, N-ethylanthranilic acid, N,N-dimethylanthranilic acid and N,N-diethylanthranilic acid; alkylthiobenzoic acids, for example, o-methylthiobenzoic acid and o-ethylthiobenzoic acid; alkoxybenzoic acids, for example, o-methoxybenzoic acid and o-ethoxybenzoic acid; and alkylsulfinylbenzoic acids, for example, o-methylsulfinylbenzoic acid and o-ethylsulfinylbenzoic acid.

Further, in the substituted benzoic acids (A) the additional substituent is preferably attached to an o-position of the benzene ring structure with respect to the carboxyl group.

This type of the substituted benzoic acids (A) are o-acylbenzoic acids o-aminobenzoic acids, o-arylbenzoic acids and o-halobenzoic acids and are preferably selected from o-benzoyl benzoic acid, 2-(p-toluoyl)benzoic acid, 2-(4-chlorophenyl)benzoic acid, anthranilic acid, N-methyl anthranilic acid o-phenylbenzoic acid, o-fluorobenzoic acid and o-chlorobenzoic acid.

In another embodiment of the method of the present invention, hetero atom-containing acyclic acids (B) having a main hydrocarbon structure having from 1 to 6 carbon atoms, a carboxyl group attached to a carbon atom in the main hydrocarbon structure and at least one additional substituent having hereto atom selected from the group consisting of sulfur and nitrogen, the hetero atom of the additional substituent being attached to a carbon atom contained in the main hydrocarbon structure and located in an α or β-position with respect to the carboxyl group, are usable as a straight-chain dimer selectivity-enhancing agent.

In the hetero (sulfur or nitrogen) atom-containing acyclic carboxylic acid (B), the additional substituent is selected from those of the formulae:

—SR$^1$, and —NR$^2$R$^3$ wherein R$^1$, R$^2$, and R$^3$ respectively and independently from each other represent a member selected from the group consisting of a hydrogen atom, alkyl groups having 1 to 15 carbon atoms, alkenyl groups having 2 to 15 carbon atoms, aryl groups having 6 to 15 carbon atoms, acyl groups having 2 to 15 carbon atoms and carboalkoxy groups having 2 to 15 carbon atoms.

The hetero atom-containing acyclic carboxylic acids (B) include those having an additional substituent selected from —SR$^1$, and —NR$^2$R$^3$ and attached to a carbon atom contained in the main hydrocarbon structure and located in the s-position with respect to the carboxyl group. This group of carboxylic acids (B) will referred to as hetero atom-containing, α-substituted acyclic carboxylic acids (B)-(i) hereinafter. The hetero atom-containing, α-substituted acyclic carboxylic acids (B)-(i) are preferably selected from, for example, acyclic α-(alkylthio)carboxylic acids, for example, (methylthio)acetic acid, (ethylthio)acetic acid, α-(methylthio)propionic acid, and α-(ethylthio)propionic acid; acyclic N-acyl-α-amino acids; for example, N-acetylglycine, N-acetylalanine, N-propionylglycine, N-propionylalanine, N-benzoylglycine and N-benzoylalanine; and acyclic N-carboalkoxy-α-amino acids, for example, N-carbomethoxyglycine, N-carbomethoxyalanine, N-carboethoxyglycine, N-carboethoxyalanine, N-carbobenzyloxyglicine and N-carbobenzyloxyalanine.

The hetero atom-containing acyclic carboxylic acids (B) include those having an additional substituent selected from —SR$^1$, and —NR$^2$R$^3$ and attached to a carbon atom contained in the main hydrocarbon structure and located in the β-position with respect to the carboxyl group. This group of carboxylic acids (B) will be referred to as hetero atom-containing, β-substituted acyclic carboxylic acids (B)-(ii), hereinafter. The hetero atom-containing, β-substituted acyclic carboxylic acids (B)-(ii) are preferably selected from, for example, acyclic β-(alkylthio)carboxylic acids, for example, β-(methylthio)propionic acid and β-(ethylthio)propionic acid; acyclic N-acyl-β-amino acids, for example, N-acetyl-β-alanine, N-propionyl-β-alanine, and N-benzoyl-β-alanine; and acyclic N-carboalkoxy-β-amino acids, for example, N-carbomethoxy-β-alanine, N-carboethoxy-β-alanine and N-carbobenzyloxy-β-alanine.

In still another embodiment of the method of the present invention, 5 to 12 membered heterocyclic carboxylic acids (C) having a 5 to 12 membered heterocyclic structure including a hetero atom selected from the group consisting of oxygen, sulfur and nitrogen atoms, and a carboxyl or carboxymethyl group attached to a carbon atom contained in the heterocyclic structure and located in an α-position with respect to the hetero atom, are usable as a straight-chain dimer selectivity-enhancing agent for the method of the present invention.

The heterocyclic structure in the 5 to 12 membered heterocyclic carboxylic acids (C) may have a single ring structure or a condensed multiple ring structure. Further, the heterocyclic structure may have at least one substituent selected from alkyl groups, aryl groups, acyl groups, alkoxyl groups and halogen atoms. The heterocyclic structure is preferably selected from 5 and 6 membered heterocyclic structures.

The heterocyclic groups may be saturated or non-saturated. In the unsaturated heterocyclic structure, at least one double bond may be located in any position in the heterocyclic structure, as far as the double bond allows the oxygen atom to be located in the α-position with respect to a carbon atom contained in the heterocyclic structure and bonded to the carboxyl group or carboxymethyl group.

The heterocyclic carboxylic acids (C) are preferably selected from the group consisting of:

(a) substituted and unsubstituted 2-furan carboxylic acids having a 5 membered heterocyclic structure in which an oxygen atom is located in the α-position with respect to a carbon atom contained in the heterocyclic structure and bonded to the carboxyl group, for example, 2-furan carboxylic acid, 3-methyl-2-furan carboxylic acid, 4-methyl-2-furan carboxylic acid, and tetrahydro-2-furan carboxylic acid;

(b) substituted and unsubstituted 2-furan acetic acids having a 5 membered heterocyclic structure in which an oxygen atom is located in the s-position with respect to a carbon atom contained in the heterocyclic structure and bonded to the carboxymethyl group, for example, 2-furan acetic acid, 3-methyl-2-furan acetic acid, 4-methyl-2-furan acetic acid, and tetrahydro-2-furan acetic acid;

(c) unsubstituted and substituted 2-thiophene carboxylic acids having a 5 membered heterocyclic structure in which a sulfur atom is located, in the α-position with respect to a carbon atom contained in the heterocyclic structure and bonded to the carboxyl group, for example, 2-thiophene carboxylic acid, 3-methyl-2-thiophene carboxylic acid and 5-methyl-2-thiophene carboxylic acid;

(d) unsubstituted and substituted 2-thiophene acetic acids having 5-membered heterocyclic structure in which a sulfur atom is located in the α-position with respect to a carbon atom contained in the heterocyclic structure and bonded to the carboxymethyl group, for example, thiophene acetic acid, 3-methyl-2-thiophene acetic acid, and 4-methyl-2-thiophene acetic acid;

(e) unsubstituted and substituted 2-pyrrolidine carboxylic acids having a 5 membered heterocyclic structure in which a nitrogen atom is located, in the α-position with respect to a carbon atom contained in the heterocyclic structure and bonded to the carboxyl group, for example, N-acetyl proline, N-propionyl proline, N-benzoyl proline, N-carbomethoxy proline, N-carboethoxy proline, N-carbopropoxy proline, and N-carbobenzyloxy proline;

(f) unsubstituted and substituted 2-piperidine carboxylic acids having a 6 membered heterocyclic structure in which a nitrogen atom is located, in the α-position with respect to a carbon atom contained in the heterocyclic structure and bonded to the carboxyl group, for example, N-acetyl-2-piperidine carboxylic acid, N-propionyl- 2-piperidine carboxylic acid, N-benzoyl-2piperidine carboxylic acid, N-carbomethoxy-2-piperidine carboxylic acid, N-carboethoxy-2-piperidine carboxylic acid, N-carbopropoxy-2-piperidine carboxylic acid and N-carbobenzyloxy- 2-piperidine carboxylic acid;

Among the above-mentioned carboxylic acids, particularly preferred ones are 2-furan carboxylic acid compounds, for example, 2-furan carboxylic acid, 3-methyl-2-furan carboxylic acid, and 4-methyl-2-furan carboxylic acids; 2-thiophene carboxylic acid compounds, for example, 2-thiophene carboxylic acid, 3-methyl-2-thiophene carboxylic acid, and 5-methyl-2-thiophene carboxylic acid; and 2-pyrrolidine carboxylic acid compounds, for example, N-acetyl proline, N-propionyl proline, N-benzoyl proline, N-carbomethoxy proline, N-carbothoxy proline, N-carbopropoxy proline, and N-carbobenzyloxy proline.

The above-mentioned straight chain dimer selectivity-enhancing carboxylic acids (A), (B) and (C), can be employed alone or as a mixture of two or more thereof.

In the method of the present invention, the straight chain dimer selectivity-enhancing agent is preferably present in a molar amount of 0.001 to 5 times, more preferably 0.001 to 2 times, the molar amount of acrylonitrile. If the straight chain dimer selectivity-enhancing agent is employed in too large an amount, the amount of β-cyanoethyl carboxylate produced as a by-product undesirably increases, the selectivity of acrylonitrile to the target dimers, and the production rate of the target dimers decreases due to a decrease in the content of acrylonitrile in the dimerization reaction system. Also, if the straight chain dimer selectivity-enhancing agent is used in too small an amount, the resultant reaction system exhibits an undesirably reduced dimerization rate of acrylonitrile.

In a preferable embodiment of the method of the present invention, acrylonitrile is dimerized in the presence of a ruthenium catalyst and in the additional presence of a straight chain dimer selectivity-enhancing agent comprising at least one member selected from the substituted benzoic acids (A) having a pKa of 1.50 to 6.0, determined in water at an ionic strength of 0 to 0.1 mole/liter at a temperature of 25° C.

EXAMPLES

The present invention will be further explained by way of the specific examples.

In the examples, the conversion of acrylonitrile and selectivities of acrylonitrile to target straight-chain acrylonitrile dimers, to propionitrile and to β-cyanoethyl carboxylate were calculated in accordance with the following equations.

$$\text{Conversion (\%) of acrylonitrile} = \frac{A_1}{A_0} \times 100 \quad (1)$$

in which $A_0$ represents a molar amount of acrylonitrile fed into a reaction system and $A_1$ represents a molar amount of consumed acrylonitrile in the reaction system.

Straight-chain acrylonitrile dimer-selectivity (%) =  (2)

$$\frac{D \times 2}{A_1} \times 100$$

in which $A_1$ is as defined above and D represents a total molar amount of the target straight-chain acrylonitrile dimers namely 1,4-dicyanobutene, 1,4-dicyanobutadiene and adiponitrile, produced in the reaction system.

$$\text{Propionitrile-selectivity (\%)} = \frac{P}{A_1} \times 100 \quad (3)$$

in which $A_1$ is as defined above and P represents a molar amount of propionitrile produced in the reaction system.

$$\text{β-cyanoethyl carboxylate selectivity (\%)} = \frac{C}{A_1} \times 100 \quad (4)$$

in which $A_1$ is as defined above and C represents a molar amount of β-cyanoethyl carboxylate produced in the reaction system.

Example 1

An autoclave made from a stainless steel, having a capacity of 100 ml and equipped with a stirrer was used as a reactor. The reactor was charged with 15.0 g (283 millimole) of acrylonitrile and then with 37.1 mg (0.0766 millimole) of dichloro-tetrakis (dimethylsulfoxide)ruthenium, 8.5 mg (0.08 millimole) of sodium carbonate and 1.07 g (7.66 millimole) of o-fluorobenzoic acid having a pKa of 3.27. The inside space of the reactor was filled with nitrogen gas, and the reaction mixture was heated to a temperature of 150° C. and then maintained at this temperature under a reaction pressure of 5 kg/cm$^2$G for 6 hours, to effect the dimerization of acrylonitrile.

The reactor was then cooled and the resultant reaction product mixture was subjected to a gas chromatographic analysis. It was confirmed that the reaction product mixture contained 12.3 g (232 millimole) of nonreacted acrylonitrile, 2.01 g (18.9 millimole) of 1,4-dicyanobutene, 0.16 g (1.5 millimole) of 1,4-dicyanobutadiene, 0.078 g (0.72 millimole) of adiponitrile, 0.083 g (1.5 millimole) of propionitrile and 0.88 g (4.6 millimole) of β-cyanoethyl o-fluorobenzoate.

From the above-mentioned analysis results, it was found that the conversion of acrylonitrile was 18%, the total selectivity of the straight-chain acrylonitrile dimers (1,4-dicyanobutene, 1,4-dicyanobutadiene and adiponitrile) was 83%, the selectivity of propionitrile was 3%, and the selectivity of β-cyanoethyl o-fluorobenzoate was 9%. These results are shown in Table 1.

Examples 2 to 16

In each of Examples 2 to 16, the same reaction and analysis procedures as in Example 1 were carried out except that o-fluorobenzoic acid was replaced by 7.66 millimole of the substituted benzoic acid as shown in Table 1.

The results are shown in Table 1.

Comparative Example 1

The same reaction and analysis procedures as in Example 1 were carried out except that the of o-fluorobenzoic acid was replaced by 7.66 millimole of m-methylbenzoic acid.

The results are shown in Table 1.

Comparative Example 2

The same reaction and analysis procedure as in Example 1 were carried out, except that o-fluorobenzoic acid was replaced by 7.66 millimoles of benzoic acid. The results are shown in Table 1.

Comparative Example 3

The same reaction and analysis procedures as in Example 1 were carried out, except that o-fluorobenzoic acid was replaced by 7.66 millimole of pentafluorobenzoic acid.

The results are shown in Table 1.

TABLE 1

| Example No. | Straight-chain dimer selectivity-enhancing agent Type | pKa | Acrylonitrile conversion (%) | Straight-chain dimer selectivity (%) | Propionitrile selectivity (%) | β-cyano-ethyl carboxylate selectivity (%) |
|---|---|---|---|---|---|---|
| Example 1 | o-fluorobenzoic acid | 3.27 | 18 | 83 | 3 | 9 |
| 2 | 2,6-difluorobenzoic acid | 2.31 | 10 | 68 | 3 | 9 |
| 3 | o-chlorobenzoic acid | 2.92 | 17 | 82 | 3 | 11 |
| 4 | m-chlorobenzoic acid | 3.82 | 17 | 80 | 3 | 12 |
| 5 | 2,6-dichlorobenzoic acid | 1.82 | 12 | 78 | 3 | 13 |
| 6 | 3,4-dichlorobenzoic acid | 3.64 | 17 | 82 | 3 | 11 |
| 7 | o-bromobenzoic acid | 2.85 | 12 | 78 | 3 | 13 |
| 8 | m-trifluoromethylbenzoic acid | 3.77 | 13 | 82 | 3 | 9 |
| 9 | m-cyanobenzoic acid | 3.60 | 13 | 70 | 3 | 22 |
| 10 | p-acetylbenzoic acid | 3.70 | 15 | 78 | 3 | 14 |
| 11 | o-acetylbenzoic acid | 3.79 | 15 | 77 | 3 | 15 |
| 12 | o-benzoylbenzoic acid | 3.54 | 18 | 85 | 3 | 9 |
| 13 | o-phenylbenzoic acid | 3.46 | 17 | 82 | 3 | 11 |
| 14 | Anthranilic acid | 4.79 | 11 | 85 | 3 | 7 |
| 15 | N-methylanthranilic acid | 5.34 | 17 | 83 | 3 | 8 |
| 16 | o-methoxybenzoic acid | 4.09 | 9 | 81 | 8 | 6 |
| Comparative Example 1 | m-methylbenzoic acid | 4.27 | 12 | 58 | 3 | 25 |
| 2 | benzoic acid | 4.21 | 12 | 60 | 3 | 22 |
| 3 | pentafluorobenzoic acid | 1.48 | 8 | 10 | 10 | 0 |

Example 17

An autoclave made from a stainless steel, having a capacity of 100 ml and equipped with a stirrer was used as a reactor. The reactor was charged with 15.0 g (283 millimole) of acrylonitrile and then with 37.1 mg (0.0766 millimole) of dichloro-tetrakis (dimethylsulfoxide)ruthenium, 22.0 mg (0.229 millimole) of sodium propionate and 982 mg (7.66 millimole) of 2-thiophene carboxylic acid. The inside space of the reactor was filled with nitrogen gas, and the reaction mixture was heated to a temperature of 150° C. and then maintained at this temperature under a reaction pressure of 5 kg/cm²G for 6 hours, to effect the dimerization of acrylonitrile.

The reactor was then cooled and the resultant reaction product mixture was subjected to a gas chromatographic analysis. It was confirmed that the reaction product mixture contained 12.0 g (226 millimole) of nonreacted acrylonitrile, 12.29 g (21.6 millimole) of 1,4-dicyanobutene, 0.21 g (2.0 millimole) of 1,4-dicyanobutadiene, 0.088 g (0.8 millimole) of adiponitrile 0.088 g (1.6 millimole) of propionitrile and 0.60 g (3.3 millimole) of β-cyanoethyl 2-thiophene carboxylate.

From the above-mentioned analysis results, it was found that the conversion of acrylonitrile was 20%, the total selectivity of the straight-chain acrylonitrile dimers (1,4-dicyanobutene, 1,4-dicyanobutadiene and adiponitrile) was 86%, the propionitrile selectivity was 3%, and the β-cyanoethyl 2-thiophene carboxylate was 6%.

These results are shown in Table 2.

Examples 18–22

In each of Examples 18 to 22, the same reaction and analysis procedures as in Example 17 were carried out except that 2-thiophene carboxylic acid was replaced by the sulfur or nitrogen-containing carboxylic acid as shown in Table 2.

The results are shown in Table 2.

Example 23

The same reaction and analysis procedures as in Example 17 were carried out except that 2-thiophene carboxylic acid was replaced by 2-furan carboxylic acid.

The results are shown in Table 2.

TABLE 2

| Example No. | Straight-chain dimer selectivity-enhancing agent | Acrylonitrile conversion (%) | Straight-chain dimer selectivity (%) | Propionitrile selectivity (%) | β-cyano-ethyl carboxylate selectivity (%) |
|---|---|---|---|---|---|
| 17 | 2-Thiophene carboxylic acid | 20 | 86 | 3 | 6 |

TABLE 2-continued

| Example No. | Straight-chain dimer selectivity-enhancing agent | Acrylo-nitrile conversion (%) | Straight-chain dimer selectivity (%) | Propio-nitrile selectivity (%) | β-cyano-ethyl carboxylate selectivity (%) |
|---|---|---|---|---|---|
| 18 | 5-Methyl-2-thiophene carboxylic acid | 11 | 86 | 3 | 6 |
| 19 | 2-Thiophene acetic acid | 11 | 68 | 3 | 6 |
| 20 | N-Carbobenzyloxyproline | 19 | 86 | 3 | 6 |
| 21 | N-Carbobenzyloxyglicine | 7 | 72 | 3 | 17 |
| 22 | N-Carbozenzyloxyalanine | 9 | 75 | 3 | 15 |
| 23 | 2-Furancarboxylic acid | 19 | 86 | 3 | 6 |

As Tables 1 and 2 clearly indicate, the method of the present invention advantageously produces straight-chain acrylonitrile dimers at a high selectivity while restricting the by-production of propionitrile, branched-chain acrylonitrile dimers and β-cyanoethyl carboxylate, due to the utilization of the specific carboxylic acids as a straight-chain dimer selectivity-enhancing agent.

We claim:

1. A method of producing straight-chain acrylonitrile dimers including 1,4-dicyano-butene, 1,4-dicyanobutadiene and adiponitrile, comprising dimerizing acrylonitrile at a temperature of 70° to 220° C. and under a pressure of from 50 mmHg to 100 kg/cm²G, in the presence of a catalyst consisting essentially of at least one ruthenium compound selected from the group consisting of ruthenium salts of inorganic salts, ruthenium slats of organic acids and ruthenium coordination compounds in which a ruthenium atom serves as a coordination center atom, and in an amount of 0.0001 to 10 molar % based on the molar amount of acrylonitrile and in the additional presence of a straight-chain dimer selectivity-enhancing agent consisting essentially of at least one member selected from the group consisting of:

(A) substituted benzoic acids having a benzene ring structure, and a carboxyl group and at least one additional substituent attached to the benzene ring structure, and selected from the group consisting of one or two halogen atoms, haloalkyl groups, a cyano group acetyl groups, benzoyl groups, carboalkoxyl groups, a phenyl group, alkoxyl groups, an amino group, N-methyl amino group, N-ethyl amino group, N,N-dimethyl amino group, N,N-diethyl amino groups, alkylthio groups and alkylsulfinyl groups;

(B) hetero atom-containing acyclic carboxylic acids having a main hydrocarbon structure with 1 to 6 carbon atoms, a carboxyl group attached to a carbon atom in the main hydrocarbon structure, and at least one additional substituent selected from the group consisting of the groups of the formula:

—SR$^1$, and —NR$^2$R$^3$ wherein R$^1$, R$^2$, and R$^3$ respectively and independently from each other represent a member selected from the group consisting of a hydrogen atom, alkyl groups having 1 to 15 carbon atoms, alkenyl groups having 2 to 15 carbon atoms, aryl groups having 6 to 15 carbon atoms, acyl groups having 2 to 15 carbon atoms and carboalkoxyl groups having 2 to 15 carbon atoms, the additional substituent being attached to a carbon atom contained in the main hydrocarbon structure and located in an α or β-position with respect to the carboxyl group; and (C) five to twelve membered heterocyclic carboxylic acids having a 5 to 12 membered heerocyclic structure including a hetero atom selected from the group consisting of oxygen, sulfur and nitrogen atoms, and a carboxyl group attached to a carbon atom contained in the heterocyclic structure and located in an α-position with respect to the hetero atom, the straight-chain dimer selectivity-enhancing agent being present in a molar amount of 0.0001 to 5 times the molar amount of acrylonitrile.

2. The method as claimed in claim 1, wherein the substituted benzoic acids (A) exhibit a pKa of 1.50 to 6.0, determined in water at an ionic strength of 0 to 0.1 mole/liter at a temperature of 25° C.

3. The method as claimed in claim 1, wherein the substituted benzoic acids (A) are selected from the group consisting of fluorobenzoic acids, chlorobenzoic acids, bromobenzoic acids, fluoroalkylbenzoic acids, chloroalkyl benzoic acids, cyanobenzoic acids, acylbenzoic acids, carboalkoxybenzoic acids, arylbenzoic acids, aminobenzoic acids, alkylthiobenzoic acids, alkoxybenzoic acids and alkylsulfinylbenzoic acids.

4. The method as claimed in claim 1, wherein in the substituted benzoic acids (A) the additional substituent is attached to an o-position of the benzene ring structure with respect to the carboxyl group.

5. The method as claimed in claim 4, wherein the substituted benzoic acids (A) are selected from the group consisting of o-acylbenzoic acids, o-aminobenzoic acid, o-aryl benzoic aids, and o-halobenzoic acids.

6. The method as claimed in claim 1, wherein the hetero atom-containing acyclic carboxylic acids (B) have an additional substituent selected from —SR$^1$, and —NR$^2$R$^3$ and attached to a carbon atom contained in the main hydrocarbon structure and located in the α-position with respect to the carboxyl group.

7. The method as claimed in claim 6, wherein in the hetero atom-containing acyclic carboxylic acids (B), the additional substituent is selected from the group consisting of alkylthio, N-acyl-α-amino, and N-carboalkoxy-α-amino groups.

8. The method as claimed in claim 1, wherein, the hetero atom-containing acyclic carboxylic acids (B) have an additional substituent selected from —SR$^1$, and —NR$^2$R$^3$, and attached to a carbon atom contained in the main hydrocarbon structure which has 2 to 6 carbon atoms, and located in the β-position with respect to the carboxyl group.

9. The method as claimed in claim 1, wherein in the 5 to 12 membered heterocyclic carboxylic acids (C), the 5 to 12 membered heterocyclic structure is selected from the group consisting of furan, thiophene and pyrrolidine structures which may be substituted with at least one substituent different from the carboxyl groups.

10. The method as claimed in claim 1, wherein the 5 to 12 membered heterocyclic carboxylic acids (C) are selected from the group consisting of unsubstituted and substituted 2-furan carboxylic acids, 2-thiophene carboxylic acids, 2-pyrrolidine carboxylic acids and 2-piperidine carboxylic acids.

11. The method as claimed in claim 1, wherein the dimerizing step is carried out in the absence of hydrogen gas.

12. The method as claimed in claim 1, wherein the ruthenium compound for the catalyst is selected from the group consisting of ruthenium chloride, ruthenium bromide, ruthenium iodide, ruthenium sulfate, ruthenium nitrate, ruthenium acetate, ruthenium propionate, ruthenium butanoate, ruthenium pentanoate, ruthenium hexanoate, ruthenium stearate, ruthenium naphthenate, ruthenium oxalate, ruthenium succinate, dichloro-tetrakis(dimethylsulfoxide)ruthenium, dichloro-tetraacrylonitrile ruthenium, dichloro-tris(triphenylphosphine)ruthenium, dichloro-tetrakis(triphenylphosphine)ruthenium and tris(dimethylsulfoxide)ruthenium di(2-thiophene carboxylate)monohydrate.

13. The method as claimed in claim 1, wherein the dimerizing step is carried out in the further presence of at least one member selected from basic compounds and reducing compounds.

14. The method as claimed in claim 13, wherein the basic compounds are selected from the group consisting of hydroxides of alkali metals, carbonates of alkali metals, hydrogen alkali metal carbonates, alkali metal salts of carboxylic acids, alkoxides of alkali metals, ammonia, monoalkyl amines, dialkyl amines, trialkyl amines, aniline, monoalkylanilines and dialkylanilines.

15. The method as claimed in claim 1, wherein the dimerizing step is carried out in the further presence of a reducing compound.

16. The method as claimed in claim 13, wherein the basic compound is present in a molar amount of 0.05 to 30 times the molar amount of the ruthenium compound catalyst.

17. The method as claimed in claim 13, wherein the reducing compound is present in a molar amount of 0.05 to 30 times the molar amount of the ruthenium compound catalyst.

18. The method as claimed in claim 1, wherein the dimerizing step is carried out without using a reaction medium.

19. The method as claimed in claim 1, wherein the dimerizing step is carried out in a reaction medium.

20. The method as claimed in claim 19, wherein the reaction medium consists of at least one member selected from the group consisting of nitrile compounds, sulfoxide compounds, ether compounds, amide compounds, ester compounds, alcohol compounds, halogenated hydrocarbon compounds, amide compounds, halogenated hydrocarbon compounds, ester compounds, alcohol compounds and water.

21. The method as claimed in claim 15, wherein the reducing compounds are selected from the group consisting of organic tin compounds, organic germanium compounds, organic silicon compounds, organic boron compounds, organic aluminum compounds, hydrogenated boron compounds, hydrogenated aluminum compounds, metal-hydrogen compounds, and metal elements.

22. The method as claimed in claim 3, wherein the substituted benzoic acids (A) is selected from the group consisting of trifluoromethylbenzoic acids, trichloromethylbenzoic acids, cyanobenzoic acids, acetyl benzoic acids, benzoylbenzoic acids, toluoylbenzoic acids, carbomethoxybenzoic acids, phenylbenzoic acids, tolylbenzoic acids, N-methylaminobenzoic acids, N-ethylaminobenzoic acids, N,N-dimethylaminobenzoic acids, N-N-diethylaminobenzoic acids, methylthiobenzoic acids, ethylthiobenzoic acids, methoxybenzoic acids, methylsulfinylbenzoic acids, and ethylsulfinylbenzoic acids.

23. The method as claimed in claim 5, wherein the substituted benzoic acids (A) are selected from the group consisting o-acetylbenzoic acids, o-benzoylbenzoic acids, o-toluoylbenzoic acids, o-N-methylaminobenzoic acids, o-phenylbenzoic acids, o-tolylbenzoic acids and o-halobenzoic acids.

* * * * *